United States Patent
Muramatsu et al.

(10) Patent No.: US 6,563,017 B2
(45) Date of Patent: *May 13, 2003

(54) IN VIVO ELECTROPORATION METHOD FOR EARLY STAGE EMBRYO OF CHICKENS

(75) Inventors: Tatsuo Muramatsu, Aichi (JP), jpx; Tsuneaki Sakata, Osaka (JP); Mamoru Hasegawa, Ibaraki (JP)

(73) Assignee: Dnavec Research Inc., Ibaraki (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,565

(22) PCT Filed: Feb. 28, 1997

(86) PCT No.: PCT/JP97/00611
§ 371 (c)(1),
(2), (4) Date: Sep. 13, 1999

(87) PCT Pub. No.: WO98/01027
PCT Pub. Date: Jan. 15, 1998

(65) Prior Publication Data
US 2002/0046414 A1 Apr. 18, 2002

(30) Foreign Application Priority Data
Jul. 8, 1996 (JP) .............................. 8-197001

(51) Int. Cl.[7] .................. C12N 15/87; C12N 15/63; C12N 15/85; C12N 15/00; A01K 67/027
(52) U.S. Cl. .................. 800/21; 435/455; 435/461; 800/19; 800/25
(58) Field of Search .................. 435/465, 455, 435/461; 800/18, 13, 25, 19, 21

(56) References Cited

PUBLICATIONS

Mullins, S1996, vol. 98, n 11, J. Clin. Invest., S37–S40.*
Lewin, Genes IV, p699.*
Hogan, Manipulating the Mouse Embryo, p252.*
Murakami, 1994, vol. 34, J. of Biotech., 35–42.*
Whitmer, 1992, vol. 6 n. 10 AIDS, 1133–8.*
Powers et al., "Electroporation as an effective means of introducing DNA into abalone (Haliotis rufescens) embryos," *Molecular Marine Biology and Biotechnology* 4(4):369–375 (1995).
Müeller et al., "Efficient transient expression system based on square pulse electroporation and in vivo luciferase assay of fertilized fish eggs," *Federation of European Biochemical Societies* 324(1):27–32 (1993).
Leopold et al., "Using electroporation and a slot curvette to deliver plasmid DNA to insect embryos," *Genetic Analysis: Biomolecular Engineering* 12:197–200 (1996).
Nemec et al., "Introduction of DNA into murine embryos by electroportion," *Annual Conference of the International Embryo Transfer Society Theriogenology* Jan. 15–17, 1989.
Translation of Mizutani et al., "Expression Of Foreign Genes In the Cells From Chicken Embryos," *Journal of the Japan Poultry Society*, Spring Conference edition, 33:10 (1996).
Murakami et al., "Micromachined Electroporation System For Transgenic Fish," *Journal of Biotechnology* 34:35–42 (1994).
Buono et al., "Transient Expression Of RSVCAT In Transgenic Zebrafish Made By Electroporation," *Molecular Marine Biology and Biotechnology* 1(4/5):271–275 (1992).
Mudgett et al., "Electroporation Of Embryonic Stem Cells For Generating Transgenic Mice And Studying InVitro Differentiation," *Methods on Molecular Biology* 48:167–184 (1995).
Muramatsu et al., "Comparison Of Three Nonviral Transfection Methods For Foreign Gene Expression In Early Chicken," *Biochemical And Biophysical Research Communications* 230:376–380 (1997).
Ramírez–Solis et al., "Gene Targeting In Embryonic Stem Cells," *Methods In Enzymology* 225:855–878 (1993).

* cited by examiner

Primary Examiner—Scott D. Priebe
Assistant Examiner—Peter Paras, Jr.
(74) Attorney, Agent, or Firm—Clark & Elbing LLP

(57) ABSTRACT

A gene is transferred to the early stage chicken embryo by electroporation with placing the electrode tips to hold both ends of the embryo. Transfer of the desired gene to the early stage embryo was detected using the β-galactosidase gene of *E coli* as a reporter gene. The expression of the gene in the early stage embryo of chicken was thus confirmed. This method for transferring a gene into undifferentiated cells is simple to implement, highly efficient in transferring a gene, and applicable to various animal species.

2 Claims, 5 Drawing Sheets

IN VIVO ELECTROPORATION METHOD FOR EARLY STAGE EMBRYO OF CHICKENS

TECHNICAL FIELD

The present invention relates to the field of genetic engineering, especially the field of gene transfer technology.

BACKGROUND ART

A transgenic animal, which is an animal integrated with a cloned gene of humans and other animals and expressing the gene within its body, is highly useful as a model animal for human genetic diseases and as an experimental animal for analyzing the function of human genes. Furthermore, it is useful in breeding domestic animals as well as in producing valuable substances on a large scale in large animals. Various techniques have been developed for producing transgenic animals. One of these techniques is exemplified by the microinjection method to directly transfer a gene to the nucleus of an oocyte with pronuclei [Bioessays 2, 221–225 (1985)]. This method has been used to successfully produce a supermouse with the rat growth hormone gene and weighing up to twice as much as the normal mouse [Nature, 300, 611–615 (1982), Science, 222, 809–814, 1983)]. However, this method has the drawback of requiring highly dexterous manipulation under a microscope. Furthermore, this method is disadvantageous in that the success rate is so low that only one to three transgenic mice can be obtained on average using 100 fertilized oocytes.

There is also a retrovirus vector method comprising integrating a gene into a retrovirus vector and infecting oocytes with the transformed vector [Virology, 157, 236–240 (1987)]. However, in spite of the high gene transfer efficiency, this method poses many problems such as its toxicity and limited host specificity, and its application to humans is meeting with difficulty.

One of the most remarkable methods for producing transgenic animals these days utilizes embryonic stem cells (ES cells) which are derived from the inner cell mass (ICM) of fertilized oocytes at the blastocyte stage and which can be maintained as undifferentiated cells in culture in vitro [Nature, 309, 225–256 (1984)]. Since this method seeks to obtain a chimera by transplanting embryonic stem cells which have been injected with a gene into blastocytes, it has the advantages of enabling the selection of transformants at the cellular stage and the efficient production of chimeras. However, the animal species from which the embryonic stem cell line has been established are still limited, limiting the application of the method. Furthermore, the process of producing chimeras is tedious due to difficulties in separating and maintaining the embryonic stem cell line.

Therefore, there has been a demand for establishing a method for producing transgenic animals, which is less toxic, simply manipulable, highly efficient in gene transfer, and applicable to a wide variety of animal species.

Another method for transferring a gene is electroporation in which repairable pores are formed on the cell membrane by applying voltage pulses and injecting DNA through the pores. This electroporation method has been used to transfer a gene to cultured animal or plant cells or to localize differentiated specific tissues [Cancer Research, 56, 1050–1055 (1996)]. However, there have been no reports on the gene transfer to undifferentiated early stage embryos.

DISCLOSURE OF THE INVENTION

An objective of the present invention is to provide an electroporation method applicable to undifferentiated early stage embryos of animals in vivo.

A method for directly transferring a gene to undifferentiated early stage embryos may be very useful for producing transgenic animals because the transferred gene is maintained in all cells differentiated from the cell into which the gene has been transferred, even after the embryo grows to an individual animal. Furthermore, the electroporation method is non-toxic, simple to implement, highly efficient in transferring a gene, and applicable to a wide range of animal species. Therefore, if this method becomes available for producing transgenic animals, it may be utilized in a wide range of technical fields such as gene therapy and breeding of domestic animals.

In an attempt to produce transgenic animals by transferring a foreign gene into animals, the present inventors utilized the early stage embryo of chicken, the origin of their somatic cells. Furthermore, the inventors used the electroporation method to transfer a gene because of its simple manipulation and high transfer efficiency in general. Transfer of the desired gene to the early stage embryo was detected using the β-galactosidase gene of *E. coli* as a reporter gene. The expression of the gene in the early stage embryo of chicken was thus confirmed, thereby completing the present invention.

The present invention relates to a method for transferring a gene to the early stage embryo of animals. More specifically, it refers to a method for transferring nucleic acid to the early stage embryo of animals which method comprises transferring nucleic acid present outside the early stage embryo to the inside thereof by instantaneously applying voltage, and, more preferably, to this method wherein the said animal is Aves.

The term "electroporation" used herein means transferring nucleic acid from the outside of a cell to the inside thereof by instantaneously applying voltage.

Voltage application in this invention is usually performed by injecting into the early stage embryo a DNA solution with an osmotic pressure adjusted to become isotonic by placing the electrode tips so as to hold both ends of the embryo. The electrode shape, voltage level, voltage duration, and the number of times voltage is applied are appropriately selected depending on various factors, especially the gene transfer efficiency and survival rate of individual animals. Usually, electroporation is performed by applying a low-voltage pulse of about 10 to 75 V, preferably about 15 to 60 V, usually twice for 25 msec to 20 times for 100 msec, preferably two times for 50 msec to eight times for 100 msec. For the early stage avian embryo in particular, the hatchability is significantly improved by opening a minimal window on the egg shell to insert electrodes before applying the voltage, removing the shell membrane, serosa covering the embryo, and a small amount of egg white, covering the embryo with the small amount of egg white again after electroporation, and tightly sealing the window on the egg shell with tape.

Although there are no particular limitations in the animal species to which a gene is transferred in this invention, Aves is most preferable because fertilized eggs can easily be treated outside of the body due to its oviparity and because it has high ovipositional capability.

The gene to be transferred is not particularly limited, and various genes can be used depending on the purpose. For example, to produce a disease model animal and analyze the function of a specific gene, it is possible to transfer a mutated gene whose base sequence is modified and an antisense gene. For gene therapy, it is beneficial to transfer a normal gene corresponding to the transformed gene or a gene for therapy. Furthermore, to observe the expression level of a particular gene and localize the expression, the gene may be transferred by directly connecting its promoter region to a suitable reporter gene. When these genes are linked to an appropriate promoter and transferred, they can be highly expressed intracellularly.

BEST MODE FOR IMPLEMENTING THE INVENTION

EXAMPLE 1

Transferring a gene to an early stage chicken embryo by in vivo electroporation

Figure 1:
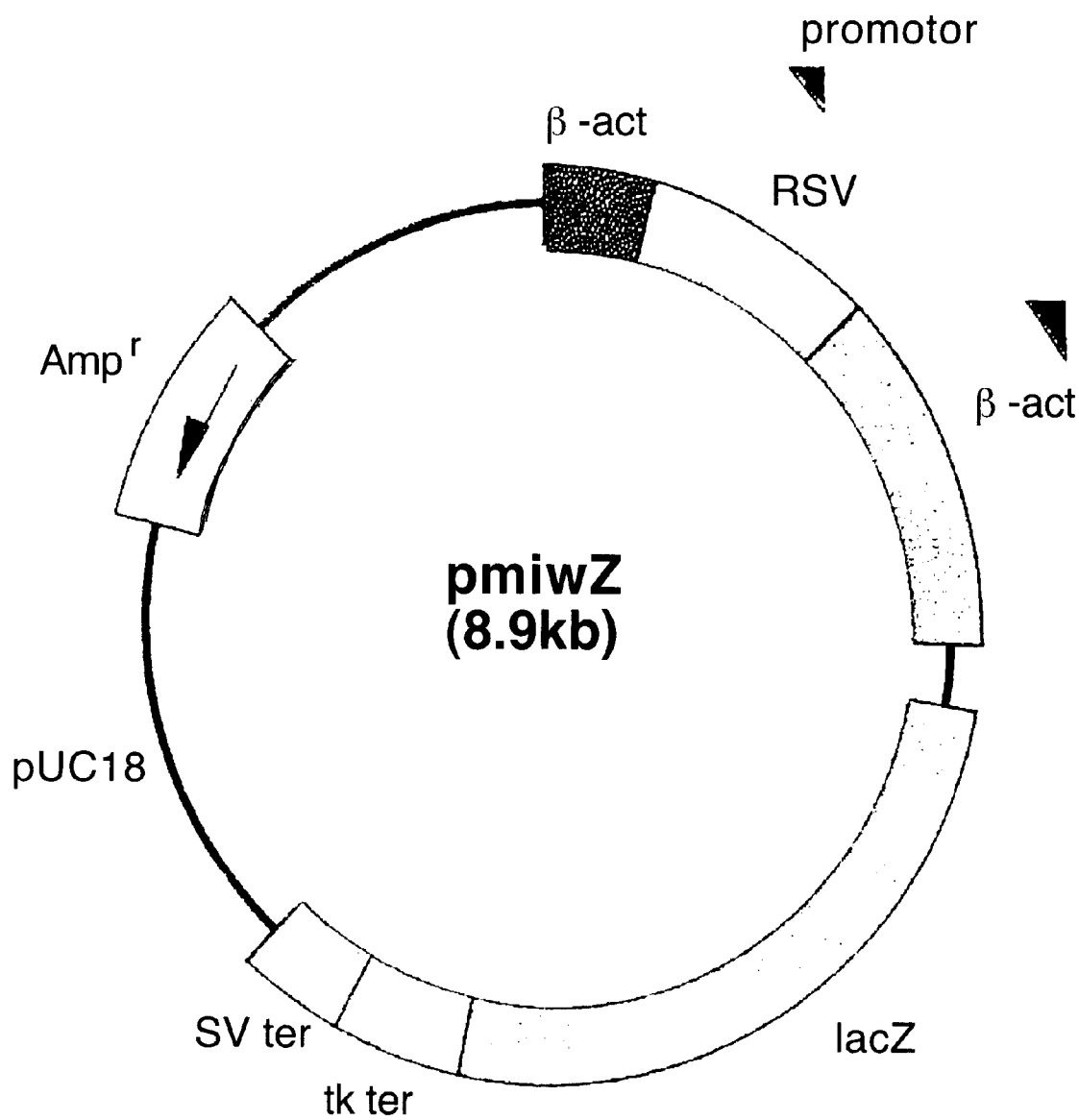
FIG. 1 shows a vector, pmiwZ, for the high-level expression of the *E. coli* lacZ (β-galactosidase) gene in mammalian cells.

After the round end of a fertilized chicken egg was sterilized with 70% ethanol, a 1 cm-diameter window was opened on the egg shell using a drill, and the shell membrane, serosa covering the chicken embryo, and the egg white were removed. A solution containing pmiwZ [1.5 μg of DNA per embryo dissolved in 10 μg of a solution containing 5 mM calcium chloride ($CaCl_2$) and 274 mM sodium chloride (NaCl)] as a DNA model was then injected quickly into the exposed chicken embryo using a glass capillary with a sharpened tip. pmiwZ is a vector for the high-level expression of the *E. coli* lacZ (β-galactosidase) gene in mammalian cells. This vector has the chicken β-actin promoter at the upstream of the lacZ gene and RSV-LTR further upstream of the gene [registered in the Japanese Cancer Resources Bank (No. VEO52)] (FIG. 1). After the injection, the chicken embryo was held between the electrodes of the electroporater and electrically pulsed three times at 25 V for 50 msec. After the electric pulse treatment, the chicken embryo was covered with egg white and the window was tightly sealed with adhesive tape. The egg was then incubated while rotating 90° every 3 h, and, 48 h after the gene transfer, the embryo was excised from the egg yolk to examine the foreign gene in it. The transferred gene was detected by staining with X-gal (5-bromo-4-chloro-3-indolyl-β-D-galactoside).

Figure 2:
FIG. 2 is a microscopic photograph showing the expression of the *E. coli* lacZ gene transferred into an early stage chicken embryo by the electroporation method.
Figure 3:
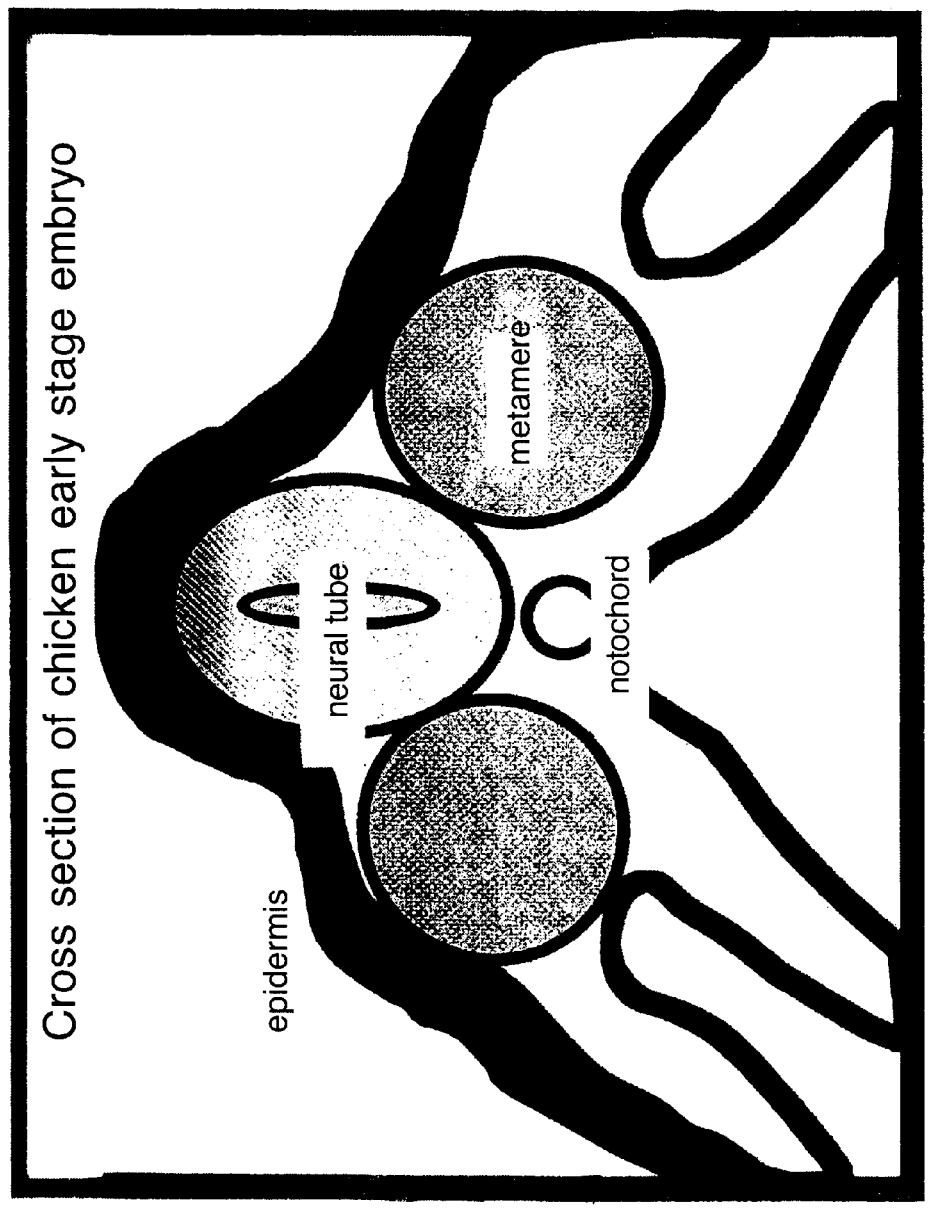
FIG. 3 is a schematic diagram depicting the cross section of the early stage chicken embryo.
Figure 4:
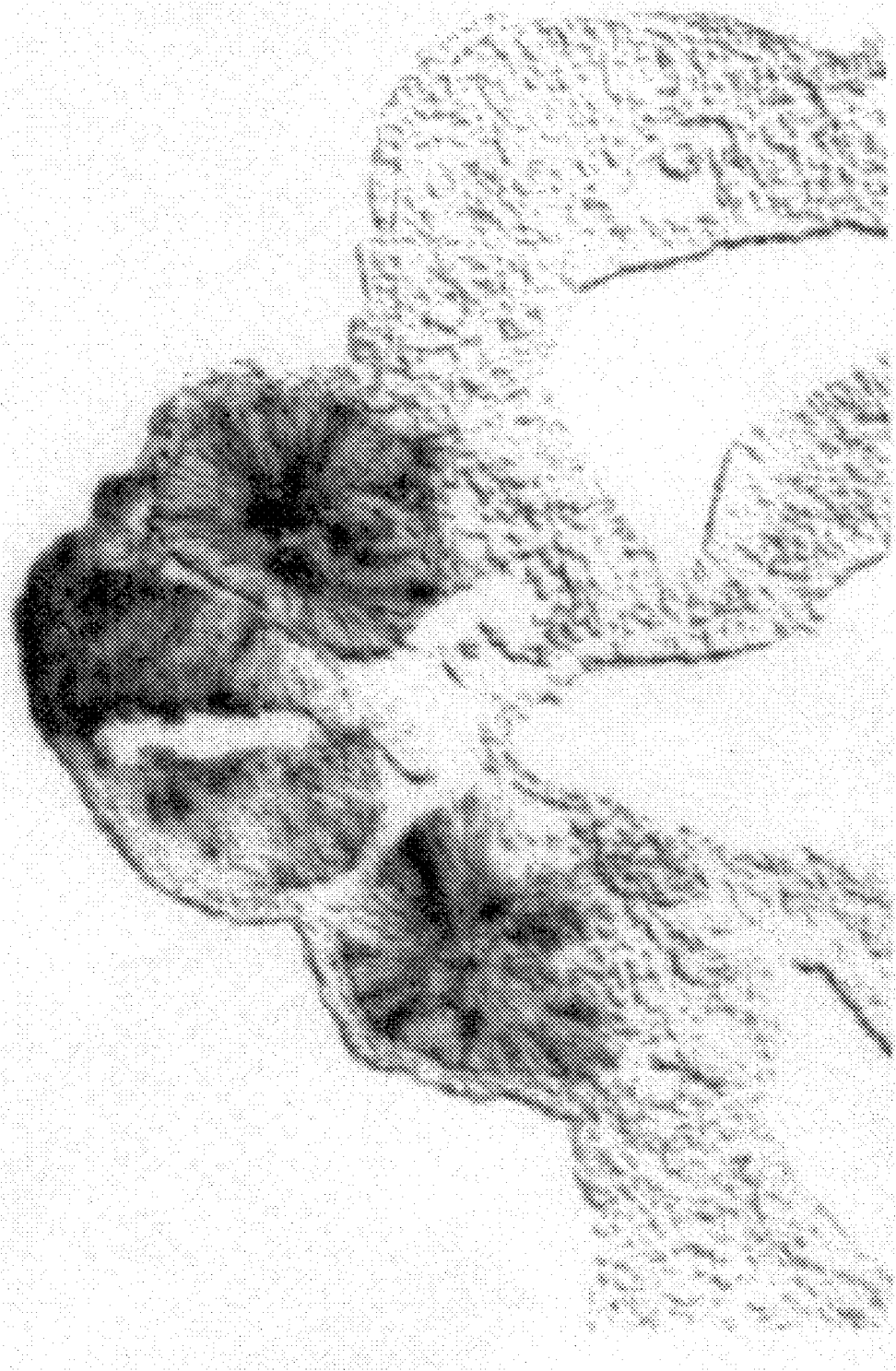
FIG. 4 is a microscopic photograph of the cross section of the early stage chicken embryo showing the expression of the *E. coli* lacZ gene transferred into it by the electroporation method.

As a result, the *E. coli* lacZ gene transferred by the electroporation method was expressed in the entire lower half of the embryo (FIG. 2). Furthermore, the expression of the lacZ gene at the neural tube and metamere was confirmed in the tissue section of the lower half of this embryo (FIGS. 3 and 4).

In this experiment, the *E. coli* lacZ gene was specifically expressed at the neural tube and metamere of the lower half of the embryo. This may be because pores were opened at the restricted sites on the cellular membrane by the electric pulse. Stable integration of DNA into a specific portion (or a lower half) of an embryo may enable specifically transferring DNA to tissues that will become primordial gonads (testis and ovary) or the egg white secretory tissue (oviduct). This will suppress the gene expression at undesirable sites and the resulting functional inhibition of individuals.

EXAMPLE 2

Effects of various voltages on hatchability and gene transfer efficiency in a chicken embryo Prior to incubation, the egg white (5 ml) was removed from the sharp end of a seed egg of the unicombed white leghorn (Aichi line) using a sterilized 20 G injection needle. The injection pore was then sealed up using a surgical alon alpha adhesive, and the hatching was initiated at 38.5° C. and 70% humidity. After 48-hour incubation, the egg was removed, and a window of about 2.5 cm in diameter was opened on the round end of the egg shell with a drill so as not to damage the egg shell membrane. To determine hatchability, only a physiological saline solution (10 μl) was injected into the chicken embryo from outside the egg shell membrane using a fine glass capillary. L-shaped electrodes having a 12 cm effective portion were placed to hold both sides of the embryo, and electroporation was performed by applying an electrical pulse from the outside of the egg shell membrane for 99 msec twice at voltages of 10 V, 25 V, 50 V, and 75 V. Immediately after the electroporation, the window in the egg shell was sealed with a plastic wrap, and the egg was incubated while being continuously rotated. To determine the gene expression level, 2 μg of a plasmid DNA (pmiwZ), into which the *E. coli* lacZ gene had been inserted, was transferred to a chicken embryo by electroporation, and the egg was kept in an incubator until it hatched. Gene expression was determined by staining with X-gal 24 hours after the electroporation.

Figure 5:
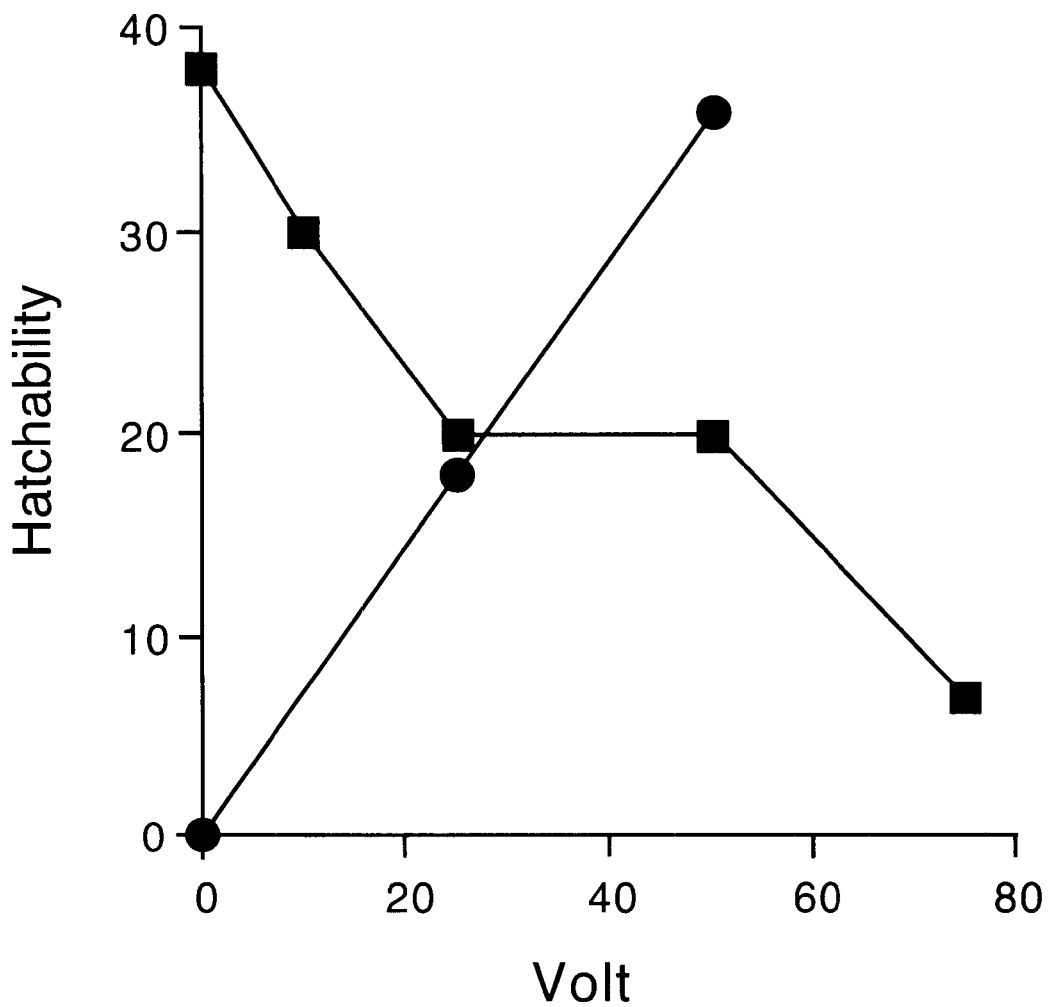
FIG. 5 is a graph showing the hatchability and gene transfer efficiency in chicken embryos for various electroporation voltages.

The results indicate that the hatchability of the chicken egg subjected to electroporation tended to decrease as the voltage increased. The highest hatchability was obtained at 10 V (9 out of 30 eggs), the second best was at both 25 V and 50 V (6 out of 30 eggs), and the lowest was at 75 V (2 out of 30 eggs) (FIG. 5). In this example, egg white was previously removed to expand the air space in the egg, which enabled performing the electroporation treatment with the egg shell membrane remaining intact. This method resulted in hatching of chicken eggs into which a foreign gene was transferred. Though hatchability decreased as the voltage was increased, the gene expression efficiency increased (FIG. 5).

INDUSTRIAL APPLICABILITY

The present invention enables transferring a foreign gene to an early stage chicken embryo. The electroporation method of this invention poses no problem of toxicity as encountered with the conventional retrovirus vector method, enables the application to a wider range of animal species than the method utilizing embryonic stem cells, and requires no special manipulating dexterity as in the microinjection method. In addition, the early stage embryo used in the present invention is the origin of somatic cells of the living body, and very effective as the target of gene transfer for producing transgenic animals. Therefore, this invention has overcome various problems in the conventional methods for producing transgenic animals and has provided a novel and very effective basic technique.

We claim:

1. A method for expressing an exogenous protein in a chicken embryo, said method comprising the steps of:
    (a) contacting said chicken embryo with a gene encoding said exogenous protein;
    (b) transferring said gene into said chicken embryo by instantaneously applying voltage to said chicken embryo; and
    (c) verifying the expression of said exogenous protein in said chicken embryo.
2. The method of claim 1, wherein said embryo to which said gene encoding an exogenous protein is transferred is an early stage embryo.

* * * * *

UNITED STATES PATENT AND TRADEMARK OFFICE
CERTIFICATE OF CORRECTION

PATENT NO.     : 6,563,017 B2
DATED          : May 13, 2003
INVENTOR(S)    : Tatsuo Muramatsu, Tsuneaki Sakata and Mamoru Hasegawa It is certified that error appears in the above-identified patent and that said Letters Patent is hereby corrected as shown below:

Title page,
Item [73], Assignee, replace "Dnavec" with -- DNAVEC --.
Item [56], References Cited, OTHER PUBLICATIONS,
"Whitmer" reference, after "vol. 6 n. 10" insert -- , --;
"Nemec et al." reference, replace "electroportion" with -- electroporation --; and
"Mudgett et al." reference, replace "InVitro" with -- In Vitro --.

Signed and Sealed this

Fifth Day of April, 2005

JON W. DUDAS
*Director of the United States Patent and Trademark Office*